United States Patent [19]
Numoto

[11] 3,968,428
[45] July 6, 1976

[54] PORTABLE SOIL MOISTURE TESTER

[76] Inventor: Minoru Numoto, 23-14, Takanawa 3 Chome, Minato, Tokyo, Japan

[22] Filed: Sept. 30, 1974

[21] Appl. No.: 510,484

[52] U.S. Cl. .............................. 324/65 R; 324/65 P
[51] Int. Cl.$^2$ .......................................... G01R 27/20
[58] Field of Search ............ 73/73; 324/65 R, 65 P, 324/65 CR, 65 CP, 158 P

[56] References Cited
UNITED STATES PATENTS

| | | | |
|---|---|---|---|
| 1,043,150 | 11/1912 | Schweitzer | 324/65 P |
| 1,910,021 | 5/1933 | Legg | 324/65 P |
| 2,437,134 | 2/1948 | Smith | 324/65 P |
| 2,461,111 | 2/1949 | Flinspach et al. | 324/65 P |
| 2,918,054 | 12/1959 | Goolkasian | 324/65 P |
| 3,306,030 | 2/1967 | Wiley | 331/111 |
| 3,689,832 | 9/1972 | Leto et al. | 324/65 R |
| 3,757,210 | 9/1973 | Hansen et al. | 324/65 CR |

FOREIGN PATENTS OR APPLICATIONS

| | | | |
|---|---|---|---|
| 1,245,942 | 1/1960 | France | 73/73 |

*Primary Examiner*—John K. Corbin
*Assistant Examiner*—Wm. H. Punter
*Attorney, Agent, or Firm*—Wegner, Stellman, McCord, Wiles & Wood

[57] ABSTRACT

A ground moisture testing and indicating device designed for quick and simple measurement of ground moisture by an untrained layman for use in connection with sowing seeds, transplanting saplings and young plants, and cultivating plants of all kinds by ascertaining the ground moisture at predetermined depths. The device is particularly useful in irrigated gardening and horticultural and agricultural farming. As conductivity of electrical current in soil varies with the content of moisture therein, the resistance of the soil is a direct function of the moisture content of the soil. The present device measures resistance of the soil at a given depth and thereby indicates the moisture of the soil at that point. A direct current voltage is generated to indicate such value by a suitable indicating device, such as a meter, a sound device utilizing a loudspeaker, or an earphone, or a visual device, such as a lamp or photodiode, etc., for detection and evaluation. The device includes a sensor at the lower end of a ground insertion rod, the sensor being connected to an electrical circuit with suitable indicating devices at the head end of the device. The ground inserting rod is provided with an adjustable depth control device for controlling the insertion whereby the soil moisture being tested may be that of the soil at the mean depth of the plant roots which is different for different plants at different stages of their growths. The head end of the testing device may be in the shape of a walking stick handle for facilitating insertion of the rod into the ground.

5 Claims, 11 Drawing Figures

FIG. 1
FIG. 2
FIG. 3
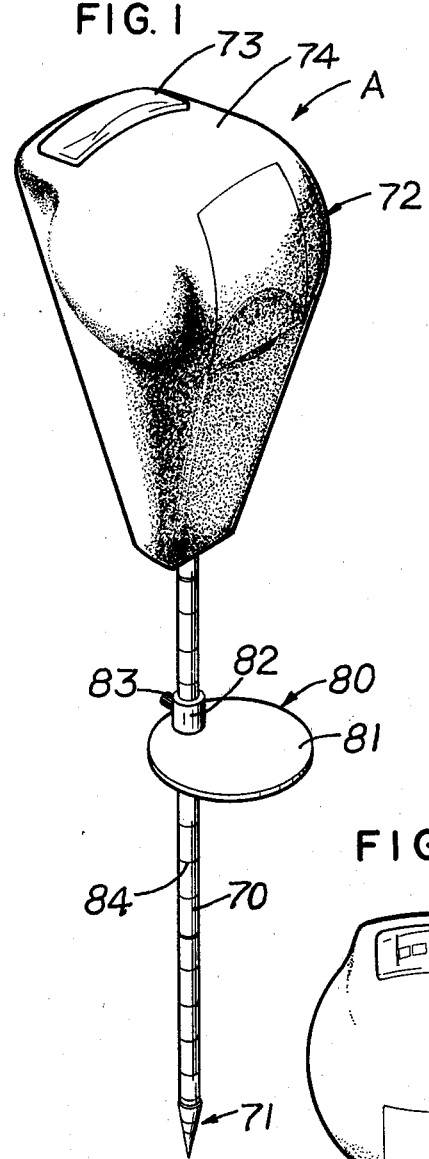
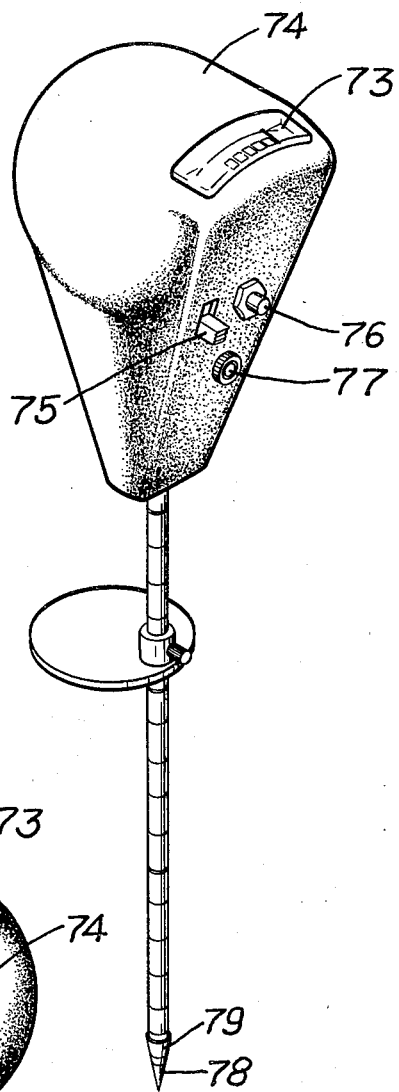
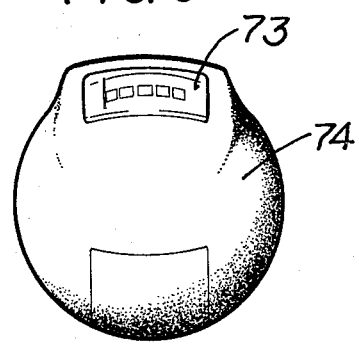

FIG. 2a
FIG. 2b
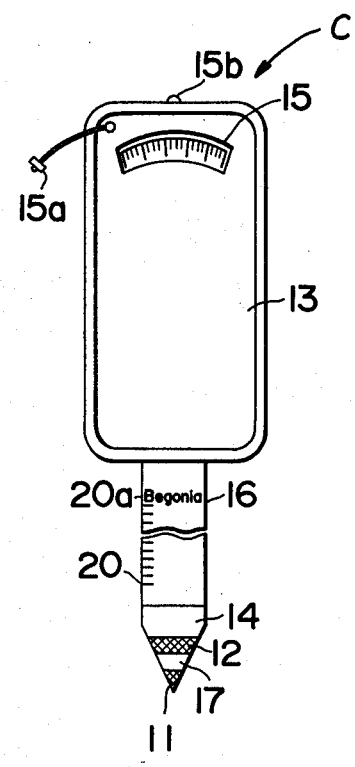
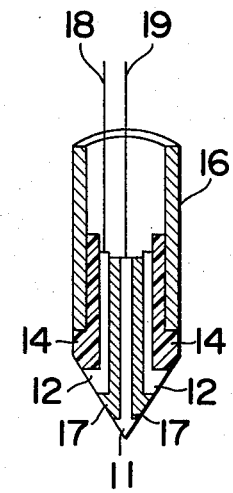

PORTABLE SOIL MOISTURE TESTER

BACKGROUND OF THE INVENTION

1. Field of the Invention

This invention relates to testing devices and in particular to devices for testing conditions of soil.

2. Description of the Prior Art

A number of different watering and irrigation devices and systems have been developed for watering flowerpots and private gardens, watering trees, plants and greens of public squares, parks, driveways, highways, and irrigating horticulture and agriculture plots in hot and arid sections of countries. However, there has been no simple device or system which can be operated by any unexperienced layman to test, ascertain and maintain a desirable state of moisture in the soil at the mean depth where seeds are to be sown, or where plants absorb the nutrition dissolved in water moisture for their growth. A number of known devices use high resistance measurement, such as direct deflection method, capacitance method, Wheatstone bridge method, etc., to provide a highly accurate reading for use in scientific experimentations. However, such devices are heavy and cumbersome and not effectively adapted for testing an area from place to place. Furthermore, such systems can be operated only by highly trained, experienced people. It is interesting to note that studies had been made and facts are known for almost all important plants as to the mean depth where each plant collects and absorbs nutritious solution from the soil through its network of roots. For instance, the depth for begonia plants is 5 cm., gladiolus or amaryllis 7 cm., dahlia 13 cm., etc. There is presently no device which is simple in operation and handy to carry about for testing the ground moisture needed by plants. Without such an instrument, almost all watering or irrigation is done at random without any direct evidence that the watering operation is what is intended. Of course, without data of the water content in the soil where it is needed, no improvement can be made scientifically.

Since the temperature, humidity of air, and the rate of air current movement in the area concerned all affect the evaporation of water in the process of irrigation, it would be extremely difficult for even men of experience to control "watering" effectively accurately and without much waste. Furthermore, geological differences of soil in one area as compared with another, and differences of geographical contours make the different rates of flow of irrigation water in different areas. Accurate testing of ground moisture is essential for effective watering or irrigation to provide the desired growth of vegetable and plant life. This invention covers a device which is very simple in operation, readily carried by hand, effectively accurate, and economically useful for horticultural applications and home gardening.

With the use of the present device, experiment data can be readily accumulated for progressive improvement in the art of horticulture and agriculture.

SUMMARY OF THE INVENTION

The present invention comprehends an improved soil tester which is simple in operation, highly portable, and economical in cost. In one form, the device is arranged in the configuration of a walking stick with electrodes at the lower end of the stick to be inserted into the soil to be tested. The inserting rod may be graduated or marked to ascertain the depth of the ground inserted for test, at which point the electrical resistance is measured between a pair of insulated electrodes and transformed by an electrical circuit to suitably indicate to the user the ground moisture. An adjustable control may be provided on the rod to limit the insertion and permit repeated tests at a fixed depth for a given plant or vegetation. The insulated electrodes are electrically connected to an electronic circuit having a battery for the power source, and indicators, such as a voltmeter, a speaker, an earphone, a lamp, or photodiode, etc., may be provided in the gripping portion of the handle.

The soil resistance between the electrodes and a fixed capacitance in the circuit produces a pulse output corresponding to the time constant of the circuit which generates a pulse oscillation by a unijunction transistor. The electronic circuit measures the frequency of pulse corresponding to the wetness or dryness of the soil under test and provides an indicating output in conformity therewith.

The invention comprehends utilizing different forms of indicating devices, such as indicating meters, earphone devices, lighting devices, such as a small lamp or photodiode, etc., to indicate soil wetness by a simple operation at economical cost, and thus is adapted for amateur use such as in testing plants and flowers in flowerpots and trough gardening.

BRIEF DESCRIPTION OF THE DRAWING

Other features and advantages of the invention will be apparent from the following description taken in connection with the accompanying drawing wherein:

FIG. 1 is a front perspective view of one device embodying the invention;

FIG. 2 is a rear perspective view of the device;

FIG. 3 is a top plan view thereof;

FIG. 2a is a broken front elevation of still another form of device embodying the invention;

FIG. 2b is a fragmentary view of the insertion electrodes thereof;

DESCRIPTION OF THE PREFERRED EMBODIMENTS

Figure 1A:
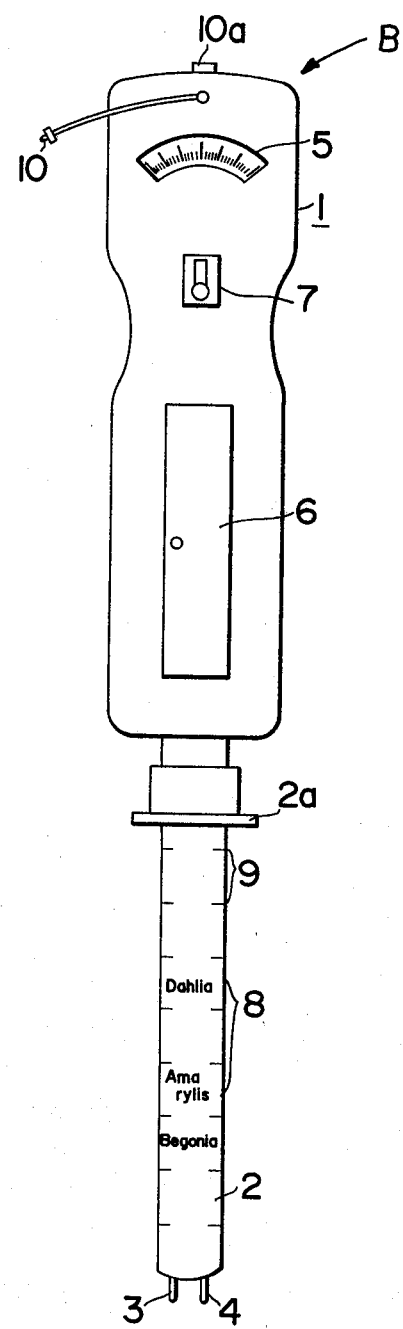
FIG. 1a is a front elevation of another form of device embodying the invention.

In the exemplary embodiment of the invention as disclosed in FIGS. 1–3 of the drawing, a soil tester, or probe, A is provided having a rod portion 70 provided with a conical tip generally designated 71. At its upper end, the rod carries a head generally designated 72 in the form of a knob-like handle adapted for facilitated grasping and manipulation of the probe by the user in making a series of soil condition tests. In making the tests, the user urges the conical tip 71 into the soil to be tested to a preselected depth and determines the condition of the soil by observing a suitable indicator which, in the embodiment of FIG. 1, may comprise a meter 73 carried in the upper surface 74 of the head for facilitated reading. The head further encloses a control circuit, such as electrical circuit P of FIG. 4, for operating the indicating means as a function of the soil condition. In illustrating the invention, the soil condition being tested comprises the wetness condition of the soil.

In the illustrated embodiment, the tester is battery operated and may be provided with a suitable switch 75 for selectively controlling On-Off of the energization power circuit of the device and testing the source voltage of the device.

As will be obvious to those skilled in the art, other indicating devices may be utilized alternatively or cumulatively to the indicating meter 73, and illustratively, may include a light emitting indicator 76, a sound producing device to be plugged into a receptacle 77, etc. As shown in FIG. 2, such additional indicating devices may be also provided in the knob portion 74 of the tester.

The probe portion of the device defines a pair of electrodes 78 and 79 which are suitably insulated from each other and from the rod 70 to provide a path for a signal to the electrical circuit P which signal is a function of the surrounding medium in which the electrodes are inserted. In the air, the high resistance of the air prevents electrical conduction between the electrodes. However, when the electrodes are inserted into the soil, a varying resistance between the electrodes occurs as a function of the wetness of the soil. This variable resistance is indicated to the user by the indicating means so as to provide an accurate indication of the soil wetness condition.

An adjustable insertion control device generally designated 80 is mounted to the rod 70 for providing repeated equal insertion of the probe into different soil samples by limiting the insertion to the adjusted amount. As shown in FIGS. 1 and 2, the insertion control device may comprise a flat plate 81 provided with a collar 82 slidably carried on rod 70 and selectively locked in adjusted position by a set screw 83. The rod may be provided with suitable indicia 84 for use in positioning the adjustable depth control 80.

In the illustrated embodiment, plate 81 comprises a relatively thick plate which may further serve as pedal means for forcibly urging the probe into the soil as by application of the user's foot downwardly thereagainst, thereby facilitating insertion of the probe into relatively hard or packed soil. The flatwise extent of the plate 81 effectively assures a positive limitation of the insertion to the desired extent in each of the series of tests to be made with the insertion control in a given adjusted position, while yet the control may be readily repositioned when desired by simple loosening and retightening of the set screw 83.

The length of the rod 70 may be as desired. For facilitated reading, the rod may be relatively long so as to place the indicator 73 at a substantial height permitting facilitated viewing thereof without stooping by the user. Alternatively, the rod may be relatively short, such as where the device is intended primarily for use with potted plants and the like.

Operation of tester A is described subsequently herein relative to the FIG. 4 wiring diagram.

Figure 1B:
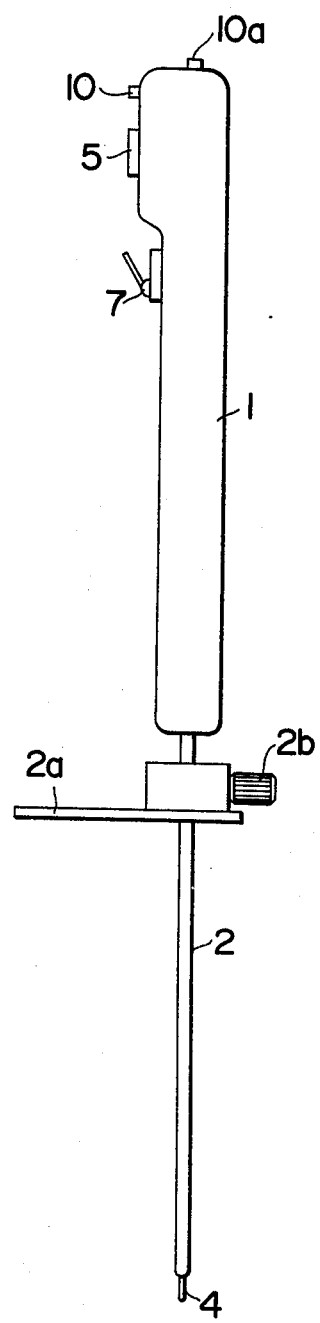
FIG. 1b is a side elevation thereof.

Referring now to FIGS. 1a and 1b, in the soil moisture tester B illustrated therein, a housing 1 has a soil inserting rod 2 fixed thereto. Rod 2 carries a pair of projecting needle electrodes 3 and 4. Electrodes 3 and 4 are connected to the electrical circuit, generally designated P, provided in the housing 1. When the rod 2 is inserted into the ground, electric pulses are generated by electrical circuit P at a frequency corresponding to the moisture content of the soil between the electrodes 3 and 4. The electric pulses are converted to a direct current signal, which corresponds to the frequency of the pulse, for indication on a voltmeter 5 provided at the top of the housing 1 to indicate to the user the moisture content of the soil. Alternatively or additionally, other indicating devices, such as an earphone or speaker 10, or light indicator photodiode 10a, etc., may be provided. The electric battery 36 shown in FIG. 4 is provided in housing 1 which may be provided with a cover 6 for easy access to the battery, and a battery switch 7. The insertion rod 2 may be marked as at 9 to indicate depths from the tip of the electrodes. The marking may, as desired, be in inches, centimeters, or other indicia 8, such as the names or figures of plants, flowers, etc., such as dahlia, amaryllis, begonia, etc., as the mean test depth of the soil for each corresponding plant. As indicated, proper moisture of the soil is vital and important for plant growth and such testing of the soil moisture content at the marked depth for a given plant permits the user to readily maintain the required state of ground moisture at such depth and thereby provide the best moisture condition for the growth.

Referring now to FIGS. 2a and 2b, another form of said moisture tester C includes a rod, or tube, 16. The rod 16 may be made of synthetic resin, or metal with or without a coating of synthetic resin, and is provided with fixed tubular electrodes 11 and 12 at a lower tip end, with insulation 17 between the electrodes 11 and 12, and insulation 14 between the electrode 12 and the wall of rod 16. As shown, the end of the insertion rod is a pointed cone with the electrodes, insulation, and the rod wall in concentric relationship, maintaining a fixed spacing between the two electrodes for accurate measurement of the soil resistance between the electrodes. The pointed configuration further provides easy insertion of the probe into the ground and avoids compaction of the soil between the electrodes in the act of insertion to prevent undesirable changing of the value of the resistance from that of the "unpacked," or natural, state soil under test. The coaxial type electrode arrangement also avoids variation of the distance between the electrodes which might occur with spaced projecting electrodes in the case of insertion thereof into hard, or packed, soil. The electrodes 11 and 12 are electrically connected by wires 19 and 18, respectively, with the electric circuit P in an upper housing 13. The indicating devices, such as meter 15, earphone 15a, or light-type indicator 15b of device C, correspond respectively, to indicators 5, 10 and 10a of the device B.

Figure 3A:
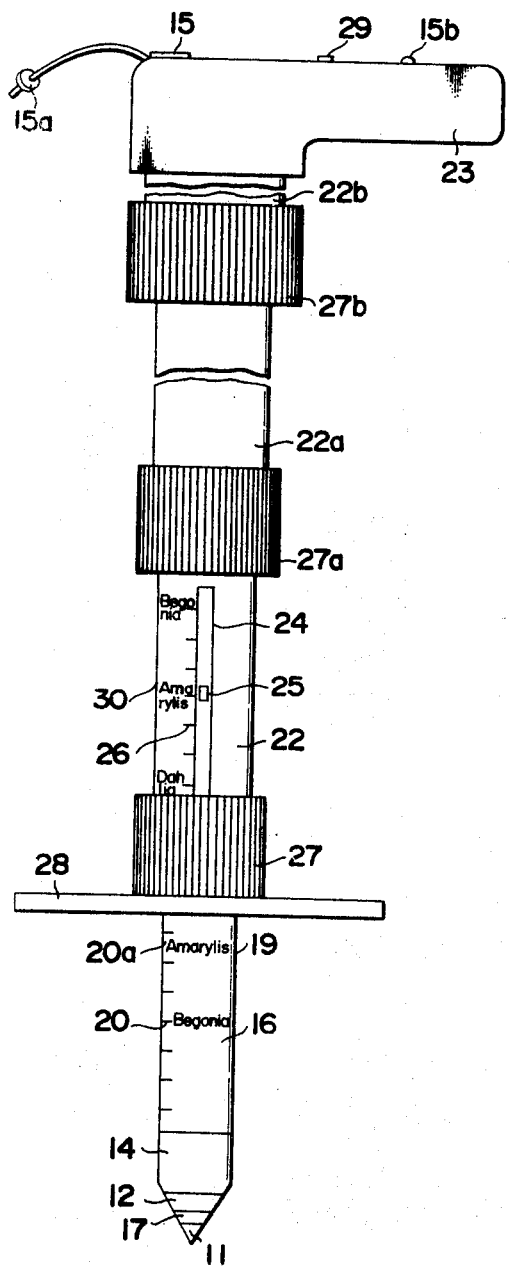
FIG. 3a is a front elevation of yet another form of the device.
Figure 3C:
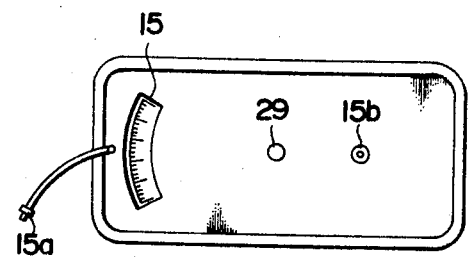
FIG. 3c is a top plan view thereof.
Figure 3B:
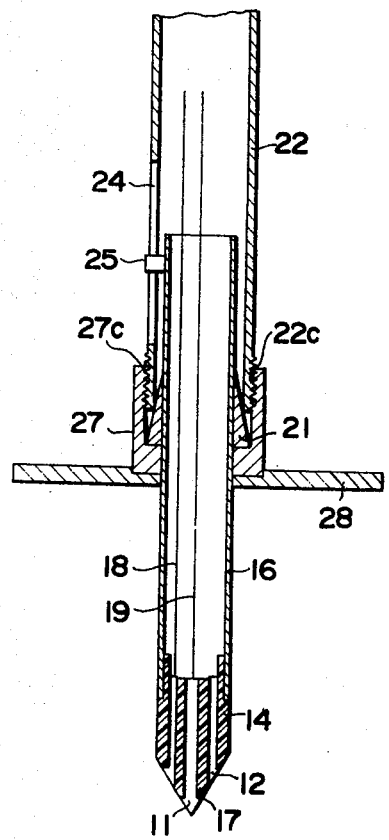
FIG. 3b is a fragmentary cross section of the insertion electrodes thereof.

Referring now to FIGS. 3a, 3b, and 3c, another testing device D includes a tubular rod 22 fixed over the insertion rod 16 with a knurled nut 27. A second tubular rod 22a is fixed over first tubular rod 22 with a knurled nut 27a. A third tubular rod 22b is fixed over second tubular rod 22a with a similar knurled nut 27b. By loosening or retightening the knurled nuts, a set of freely extensible and contractible rod elements is provided to suit the length desired by the user. The adjustably extensible rod may include any suitable number of separate elements to suit the required length.

A control disc 28 is fixed to the lower part of nut 27 for movement therewith for fixing the depth of insertion to a predetermined depth for repeated similar soil tests. Tubular rod 22, nut 27 and disc 28 may be moved up and down together by means of the connection provided by the screw thread 27c on the inside surface of the nut 27, and the screw thread 22c on the lower end of tube 22. To firmly fix the insertion rod 16 to tube 22 and nut 27, a ring-type wedge 21 is further provided.

Similar wedges may be provided between nut 27a and tube 22a, as well as nut 27b and tube 22b. Rod 16 may be provided with a small projecting pin 25 which moves up and down an elongated guide groove 24 in tube 22 to prevent rod 16 from dropping from the assembly when nut 27 is loosened.

On insertion rod 16 and on tube 22 at the end of the guide groove 24, depth marks 20 and 26, or names of plants 20a and 30, may be marked to indicate the proper depth at which soil moisture for each named plant should be tested. Marks 20a and 20 on rod 16 may be used to fix the disc 28 for required depth. The marks on tube 22 along the guide groove 24 cooperate with projection pin 25 to indicate the depth by inspection after the rod is inserted into the ground.

The upper end of the tubular shaft 22b is connected to a housing 23 which, as shown, may be in the shape of a handle. The handle encloses the electrical circuit with a suitable electrical battery for circuit operation and the indicating devices, such as meter 15, earphone 15a, lamp or photodiode 15b, etc. An electrical switch 29 is provided for operating the device. Electrical circuit P is connected to the electrodes 11 and 12 by electrical conducting wires 19 and 18. Electrodes 11 and 12 are insulated from each other and wall of rod 16 by insulators 17 and 14 similarly as in device C.

Figure 4:
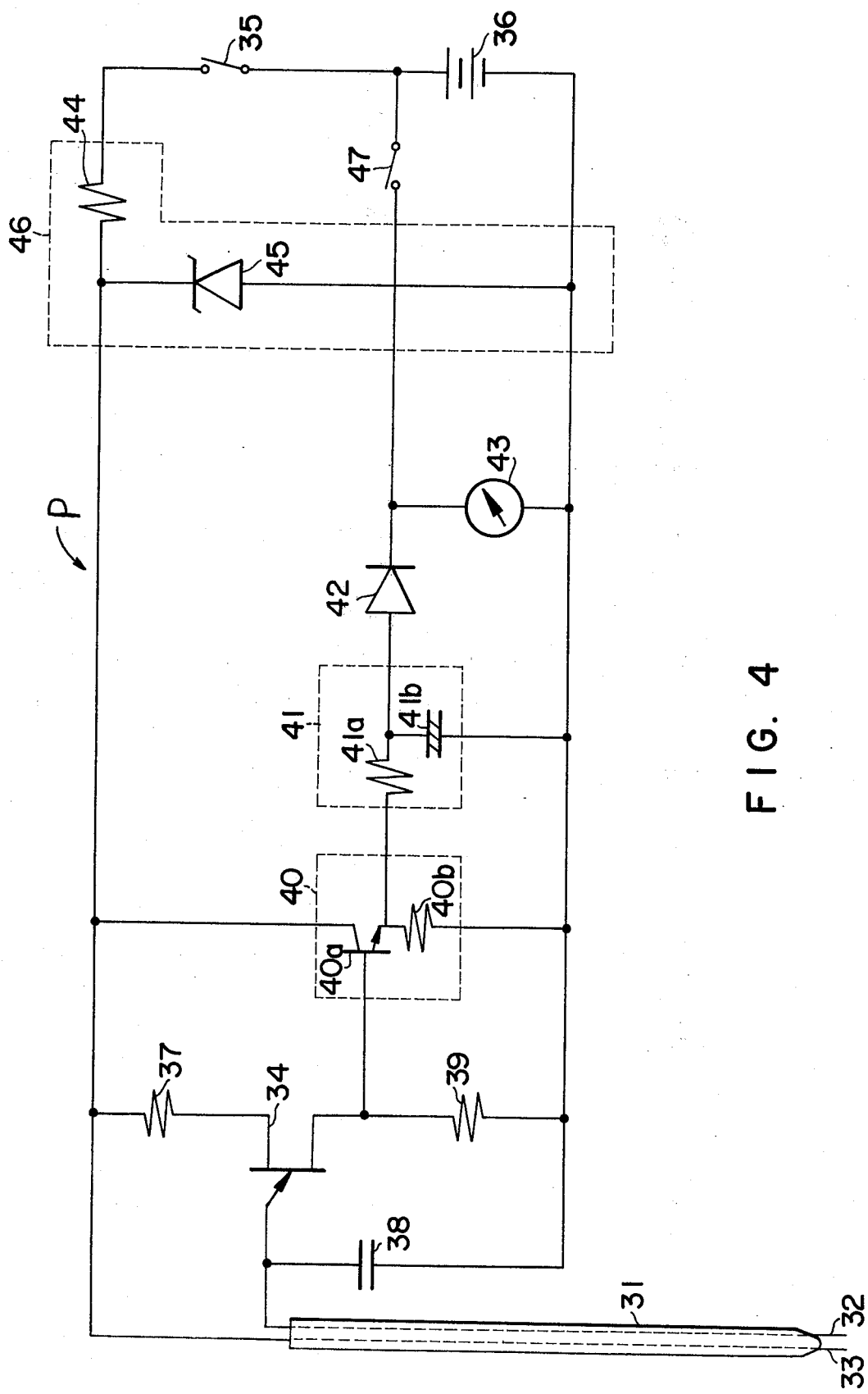
FIG. 4 is an electric circuit diagram of the control of the invention.

Referring now to FIG. 4, an electrical circuit P for use with each of the different illustrative embodiments A, B, C and D of the tester structure is illustrated. New numbers are given to corresponding elements of the devices A, B, C and D to facilitate universality understanding of the control relative to the different specific arrangements of the test structures.

Of the electrodes, identified as 32 and 33 in FIG. 4, at the end of the insertion rod 31 thereof, one electrode 32 is electrically connected with the emitter of a unijunction transistor 34 and the other electrode 33 is connected in one path through an On-Off power switch 35 to the positive terminal of a battery 36 and in a second path, through a resistor 37 to the second base of transistor 34. The emitter of transistor 34 is connected to the negative terminal of battery 36 through a condenser 38, and the first base of transistor 34 is connected likewise through a resistance load 39 to the battery.

When the electrodes 32 and 33 are inserted into ground, the resistance, corresponding to the ground moisture at the electrodes, completes the electrical circuit, connecting the emitter of transistor 34 to the positive terminal of battery 36. The resistance between the electrodes, and the capacitance of the condenser 38, determine a time constant for charging the condenser 38. When the condenser is charged to a preselected voltage, transistor 34 becomes conductive and permits condenser 38 to discharge. The seriatim charge and discharge of the condenser 38 repeated at intervals corresponding to the RC time constant, causes a pulse oscillation to be generated. The smaller the soil resistance between the electrodes, the higher the frequency of the oscillation obtained. When these pulses provide an audible signal, the total resistance, hence the moisture content of the soil between the electrodes 32 and 33, can be judged as a function of the sound frequency.

Alternatively, the pulsed signal obtained at the resistance load, or resistors 39 is converted to a DC signal having a voltage corresponding to the frequency of the pulse. For this purpose, output at the resistor 39 is shaped into a fixed band of a fixed amplitude pulse in a uniform shaping circuit 40 including a transistor 40a and a resistor 40b. This output is passed through an integration circuit device 41 including a resistor 41a and an electrolytic capacitor 41b defining a low pass filter, to provide a DC output voltage corresponding to the frequency of the output from device 40. This DC voltage is applied to DC voltmeter 43 through a diode 42 to provide a reading directly corresponding to the resistance of the soil between the electrodes. A resistance 44 and a Zener diode 45 are connected to form a constant voltage circuit portion 46 to regulate the voltage output of the battery 36. The regulated power supply voltage is applied to the oscillation circuit including transistor 34 to provide high accuracy in the use of the device. An auxiliary circuit is provided by switch 47 selectively connecting voltmeter 42 to the battery 36 to test the condition of the battery before a soil test. As will be obvious to those skilled in the art, a programmable unijunction transistor may be used as the active element of the oscillation circuit to operate at a low voltage suitable to the measurement of very low moisture contents of the soil, as in connection with grains, such as corn, maize, etc. Such use of the test device may be then considered effectively as a measurement of the "dryness" condition of the soil.

In one embodiment of the invention, the circuit elements had the following parameters:

| | |
|---|---|
| Transistor 34 | Motorola 2N4870 or 2N4871 |
| Transistor 40a | Motorola 2N4123 or 2N4124 |
| Zener Diode 45 | Motorola 1N754 or 1N755 |
| Diode 42 | Motorola 1n4001 or PS005 |
| Battery 36 | 8–10 volt battery |

The foregoing disclosure of specific embodiments is illustrative of the broad inventive concepts comprehended by the invention.

I claim:

1. In a test device for testing a condition of soil, said device including a probe having a tip adapted to be inserted into soil to be tested, spaced electrode means at said probe tip, and adjustable means for limiting the insertion of said tip into the soil to any one of a plurality of preselected depths, the improvement comprising: battery operated circuit means connected to said electrode means including a waveform shaping circuit for applying a pulsed accurately regulated voltage between said electrode means to cause a pulsed current flow, the frequency of which varies as a function of the resistance between said electrode means, and means including an integration circuit for producing a direct current the voltage of which corresponds to the resultant frequency of said pulsed current flow between said electrode means; and a direct current voltmeter responsive to said direct current to provide an accurate indication of the soil resistance between the inserted probe electrode means at said preselected depth.

2. The soil condition testing device of claim 1 wherein said circuit means includes a capacitor defining with the soil resistance a variable RC circuit providing a variable frequency of charge and discharge of said capacitor by said battery.

3. The soil condition testing device of claim 1 further including means on said probe for selectively indicating the no load voltage of said battery.

4. The soil condition testing device of claim 1 wherein said voltmeter comprises a low cost, low sensitivity voltmeter.

5. The soil condition testing device of claim 1 wherein said circuit means includes a direct current power supply battery, means for converting the output of said battery to said pulsed voltage to be applied to said electrode means including a capacitor and defining with the variable soil resistance a variable RC circuit providing a variable frequency of charge and discharge of said capacitor by said battery, and a Zener diode connected in parallel with said capacitor to provide an accurately maintained voltage application by said battery thereto.

* * * * *